(12) United States Patent
Shi

(10) Patent No.: US 8,740,924 B2
(45) Date of Patent: Jun. 3, 2014

(54) SAFE SIMPLE DISPOSABLE AUTOMATIC BLOOD LANCET

(75) Inventor: Guoping Shi, Jiangsu (CN)

(73) Assignee: Sterilance Medical (Suzhou) Inc., Suzhou (CN)

( * ) Notice: Subject to any disclaimer, the term of this patent is extended or adjusted under 35 U.S.C. 154(b) by 398 days.

(21) Appl. No.: 13/158,832

(22) Filed: Jun. 13, 2011

(65) Prior Publication Data

US 2011/0276074 A1 Nov. 10, 2011

Related U.S. Application Data

(63) Continuation of application No. PCT/CN2009/000371, filed on Apr. 3, 2009.

(30) Foreign Application Priority Data

Dec. 30, 2008 (CN) .......................... 2008 1 0136675

(51) Int. Cl.
*A61B 17/32* (2006.01)

(52) U.S. Cl.
USPC ........................................................ 606/182

(58) Field of Classification Search
CPC ............. A61B 5/1411; A61B 5/15142; A61B 5/150412; A61B 5/15117
USPC .................................................. 606/181, 182
See application file for complete search history.

(56) References Cited

U.S. PATENT DOCUMENTS

| | | | |
|---|---|---|---|
| 6,053,930 A | | 4/2000 | Ruppert |
| 6,136,013 A | * | 10/2000 | Marshall et al. .............. 606/167 |
| 7,322,997 B2 | | 1/2008 | Shi |

(Continued)

FOREIGN PATENT DOCUMENTS

| | | |
|---|---|---|
| CN | 2705119 Y | 6/2005 |
| CN | 2706129 Y | 6/2005 |

(Continued)

OTHER PUBLICATIONS

International Search Report for International Patent Application No. PCT/CN2009/000371, mailed on Sep. 10, 2009 (w/ English translation).

(Continued)

*Primary Examiner* — Thomas McEvoy
*Assistant Examiner* — Julie A Szpira

(57) ABSTRACT

A safe simple disposable automatic blood lancet includes a casing, a lancet core, a spring and a protective bar. The ejection cavity is provided inside with a space that allows the push arm to move downwards; the protective bar is provided at the end inside the ejection cavity with a safety action portion; with the protective bar assembled, this safety action portion occupies the space in the X, Y or Z direction, so as to prevent the barb from being self-locked with the self-locking barb with the push arm moving downwards; with the protective bar disassembled, this safety action portion withdraws from the space, so as to allow the barb to be self-locked with the self-locking barb with the push arm moving downwards. The lancet core can be assembled into the locking state of ready for ejection; the blood lancet can be placed into the ejection state just by twisting off the protective bar during application, and into the locking state automatically after ejection so as to be unreusable.

9 Claims, 10 Drawing Sheets

(56) References Cited

U.S. PATENT DOCUMENTS

2005/0234487 A1* 10/2005 Shi .............................. 606/181
2006/0058828 A1* 3/2006 Shi .............................. 606/181
2006/0178686 A1 8/2006 Schraga

FOREIGN PATENT DOCUMENTS

| CN | 2737303 Y | 11/2005 |
| CN | 1846612 A | 10/2006 |
| CN | 101444428 A | 6/2009 |

OTHER PUBLICATIONS

Office Action issued in Chinese Patent Application No. 2008101366753 dated Oct. 16, 2009 (with translation).

* cited by examiner

SAFE SIMPLE DISPOSABLE AUTOMATIC BLOOD LANCET

This is a Continuation of International Patent Application No. PCT/CN2009/000371 filed Apr. 3, 2009, which claims the benefit of Chinese Patent Application No. 200810136675.3 filed Dec. 30, 2008. The disclosures of the prior applications are hereby incorporated by reference herein in their entirety.

FIELD OF THE INVENTION

The present invention belongs to the field of medical apparatus technology, and particularly relates to a disposable automatic blood lancet. This blood lancet can be used simply after just twisting off the protective bar; and it can be placed into a self-locking state after ejection by locking the button through the casing engaged with the button, thus attaining the purpose of making the blood lancet unreusable.

BACKGROUND OF THE INVENTION

The disposable automatic blood lancet, as the main development stream of the current blood lancet, has been improved and developed constantly for many years. The Chinese patent once announced on Jun. 22, 2005 to authorize a utility model patent titled "Casing Self-Locking Disposable Safe Automatic Blood Lancet" with a patent number of 200420026368.7 and an announcement number of CN2705119Y (with this patent enjoying the right of priority, an American patent is applied for afterwards with a patent number of U.S. Pat. No. 7,322,997B2). In this patent, a casing forms an ejection cavity with a pinhole, a lancet core is arranged inside the ejection cavity, and an ejection structure is formed including a spring and a bayonet ejection structure. A button is arranged on the casing; and a self-locking structure is formed by a barb on the button engaged with a self-locking opening on the casing. When the button is pushed, the bayonet ejection structure will be triggered to make the lancet core disengaged from the casing, and then the spring will push the lancet core to eject. After the ejection, because of the movement of the button, the barb moves forward beyond the self-locking opening; therefore, the barb is locked at the self-locking opening in the rebounding process, and cannot go back to the pre-ejection state, making the bayonet ejection structure fail and unreusable. This design is compact in structure and skillful in concept, and particularly it can make the blood lancet enter the self-locking state after ejection by locking the button through the casing engaged with the button, thus attaining the purpose of making the blood lancet unreusable. However, it can be seen from specification or drawings of this patent that the following two operation actions have to be done before using this blood lancet: First the protective bar has to be pushed to make the lancet core compress the spring and blocked at the bayonet ejection structure; and then the protective bar has to be twisted off to make the lancet core enter the ejection state. Considering facilitating application by the medical care personnel, the fewer the operation actions the better. As for this patented product, the protective bar can be assembled into a post-push state during assembly in the manufacturing companies so as to reduce number of the operation actions. However, this will then result in a hidden trouble with the blood lancet, since even if the protective bar is not twisted off, the bayonet ejection structure may be triggered through the button during transportation and before application. This is also the first problem with this patented product. The second problem is that when the medical care personnel use this blood lancet for the first time, they may not read the operation instruction in detail, and may twist off the protective bar during application without pushing the protective bar first, which will also make the blood lancet fail to be ejected due to the blood lancet not being blocked into the bayonet ejection structure. Therefore, the purpose of the present invention is to resolve these problems.

CONTENTS OF THE INVENTION

The present invention provides a safe simple disposable automatic blood lancet, so as to resolve the following two problems with the patented product as described above: The first problem is that the patented product is not so simple due to requiring too many operation actions; and the second problem is that the patented product is inclined to be operated incorrectly. To make this patented product more advanced in technology and simpler in operation is the purpose of the present invention.

In order to attain the above purpose, the present invention adopts the following technical solution: A safe simple disposable automatic blood lancet is provided, including a casing, a lancet core and a spring;

the casing forms an ejection cavity, which is provided at one end with a pinhole; a lancet core is arranged inside the ejection cavity, and provided at one end with a protective bar, one end of which is protruded out of the pinhole of the casing; the lancet core is provided inside with a needle, a needle point of which is located inside the protective bar and oriented towards the pinhole; the protective bar and the lancet core are connected by muff-coupling or via a neck that can be twisted broken to enable a demountable connection; and the spring is arranged at the other end of the lancet core, thus forming an ejection structure with which the spring can push the lancet core to move;

the casing extends into the ejection cavity to form a flexible arm used for locking the lancet core; and the lancet core is provided with a bayonet corresponding to this flexible arm, which is engaged at the end with the bayonet, thus forming a locking structure in a ready-for-ejection state that will appear after the lancet core compresses the spring;

the casing is provided with a trigger button, which is formed by an extension on the casing or an independent member mounted on the casing; and the trigger button is provided with a push arm, which transversely passes through the ejection cavity to get close to or in touch with the end of the flexible arm, thus forming a push-type trigger structure; and the trigger button is provided on the push arm with a barb; the casing is provided with a self-locking barb corresponding to the barb, which is located in downward path of the barb; and a self-locking structure can be formed by the barb engaged with the self-locking barb after the trigger button is pushed once.

This blood lancet is innovative in the following aspects: The ejection cavity is provided inside with a space that allows the push arm to move downwards, the Z direction of the space being defined as a direction along which the push arm moves downwards and the X direction parallel to axis of the needle; the protective bar is provided at the end inside the ejection cavity with a safety action portion; with the protective bar assembled, this safety action portion occupies the space in the X, Y or Z direction, or simultaneously in arbitrary two of the X, Y and Z directions, and prevents the push arm from moving downwards to drive the barb to be self-locked with the self-locking barb; with the protective bar disassembled, this safety action portion withdraws from the space and allows the push arm to move downwards to drive the barb to be self-locked with the self-locking barb; and thus a safety structure of the trigger button is formed.

The relevant contents of the above technical solution will be explained as below:

1. In the above solution, in order to describe direction of the "space" clearly, the Z direction is defined as a direction along which the push arm moves downwards and the X direction parallel to axis of the needle, and the Y direction of the "space" thus obtained is perpendicular to the X and Z directions. This will be understood with reference to the coordinate directions as shown in FIGS. 2, 12, 15, 16, 21 and 22 in the examples.

2. In the above solution, the "space" can be understood with reference to the area circled by the double dotted line as indicated by the reference number 17 in FIGS. 2, 15 and 21 in the examples.

The present invention has the following design concept and operational principle: The present invention, based on the structural design of the Chinese patent CN2705119Y or the U.S. Pat. No. 7,322,997B2, is provided additionally with a safety action portion structure at the end of the original protective bar; with the protective bar assembled, the space inside the ejection cavity in which the push arm can be pushed to move downwards is occupied by the safety action portion to prevent the push arm from moving downwards; with the protective bar disassembled, this safety action portion withdraws from the space, allowing the push arm to move downwards. The present invention can assemble the lancet core of the blood lancet into the ready-for-ejection state for reducing number of the operation actions, while in this state the blood lancet is inclined to be ejected incorrectly to cause the blood lancet failure; with this measure, however, the incorrect ejection can be prevented so as to realize the safety protection function, thus attaining the dual purposes of simplifying operation and preventing incorrect operation.

With the technical solutions as described above, the present invention has the following advantages and effects compared with the prior art:

1. Compared with the prior art, the present invention can make the blood lancet enter the ejection state just by twisting off the protective bar. However, the following two operation actions are needed for the products described in the Chinese patent CN2705119Y or the U.S. Pat. No. 7,322,997B2: First the protective bar has to be pushed to make the lancet core compress the spring and blocked at the flexible arm; and then the protective bar has to be twisted off to make the lancet core enter the ejection state. Obviously, the present invention is simpler in operation.

2. The present invention allows the lancet core to be assembled into the locking state of ready for ejection during manufacture of the blood lancet. In this state, since the protective bar is not disassembled, and the safety action portion at its end places the trigger button in a safety protection state, there will be no incorrect ejection problem.

3. The blood lancet of the present invention can make the trigger button enter the self-locking state after usage, and thus cannot be reused. Besides, the needle point withdraws back into the casing automatically after usage and will not be exposed to the outside, guaranteeing safety of the blood lancet.

In summary, the present invention develops advantages of the Chinese patent CN2705119Y or the U.S. Pat. No. 7,322, 997B2, and overcomes their shortcomings, making this improved product fully attain the purpose of more advanced technology, simpler operation, and safer application.

List of reference numbers: 1. Casing; 2. lancet core; 3. spring; 4. protective bar; 5, ejection cavity; 6. pinhole; 7. needle point; 8. flexible arm; 9. bayonet; 10. trigger button; 11. push arm; 12. barb; 13. self-locking barb; 14. needle; 15. core pillar; 16. safety foot; 17, space; 18. neck; 19. connection rib; 20. safety jacket; 21. safety wing; and 22. safety bolt.

DETAILED DESCRIPTION OF THE EMBODIMENTS

The present invention will further be described below with reference to drawings and embodiments.

Example 1

A Safe Simple Disposable Automatic Blood Lancet

Figure 1:
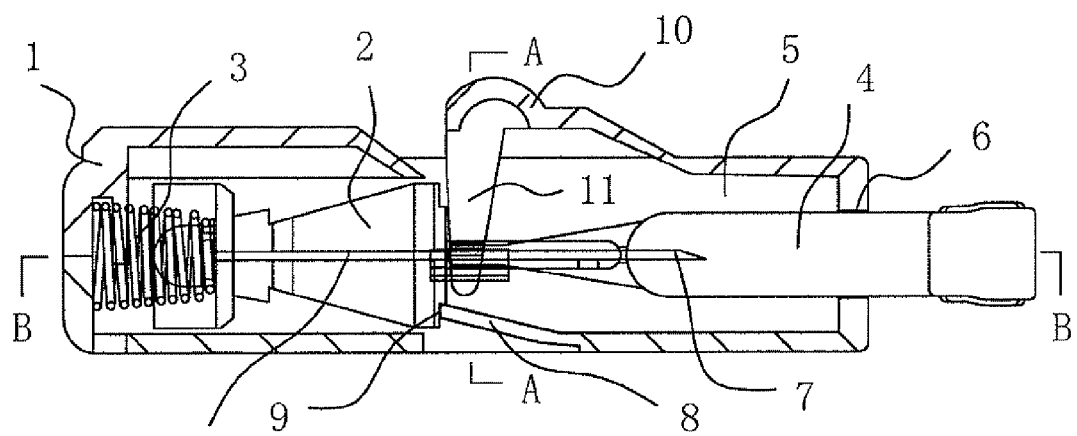
FIG. 1 is a front view of the product according to Example 1 of the present invention in the assembly state.
Figure 2:
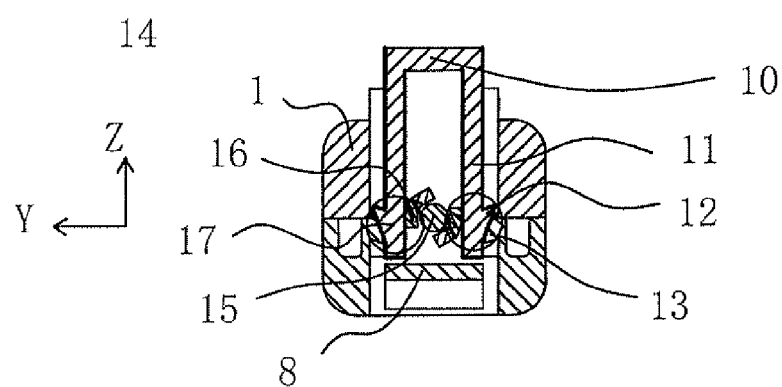
FIG. 2 is a sectional view along the line A-A of FIG. 1.
Figure 3:
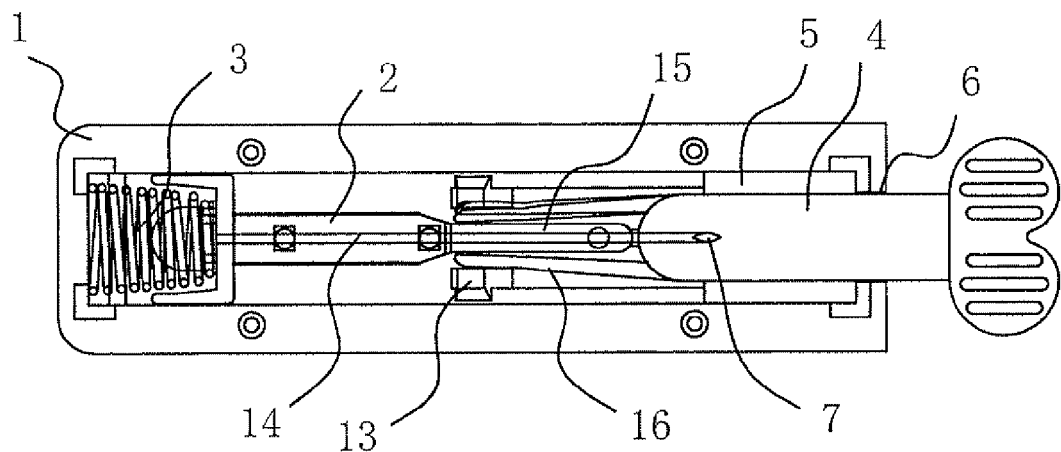
FIG. 3 is a sectional view along the line B-B of FIG. 1.

As shown in FIGS. 1-3, this blood lancet is composed of a casing 1, a lancet core 2, a spring 3 and a protective bar 4. The casing 1 is divided into two parts top and bottom, both of which are connected to form an integral structure through pin and hole structures provided on the contact surface. The casing 1 forms an ejection cavity 5, which is provided at one end with a pinhole 6. The lancet core 2 is arranged inside the ejection cavity 5 and provided at one end with a protective bar 4, one end of which is protruded out of the pinhole 6 of the casing 1. The lancet core 2 is provided inside with a needle 14, a needle point 7 of which is located inside the protective bar 4 and oriented towards the pinhole 6. The protective bar 4 and the lancet core 2 are connected by muff-coupling or via a neck 18 that can be twisted broken to enable a demountable connection. The spring 3 is arranged at the other end of the lancet core 2, thus forming an ejection structure with which the spring 3 can push the lancet core 2 to move.

The casing 1 extends at the lower part into the ejection cavity 5 to form a flexible arm 8 used for locking the lancet core 2. The flexible arm 8 is slantly arranged towards inside of the ejection cavity 5. The lancet core 2 is provided at the lower part with a bayonet 9 corresponding to this flexible arm 8, which is engaged at the end with the bayonet 9, thus forming a locking structure in a ready-for-ejection state that will appear after the lancet core 2 compresses the spring 3.

The casing 1 is provided at the upper part with a trigger button 10, which is formed by an extension on the casing 1 or an independent member mounted on the casing 1. The trigger button 10 is provided with a push arm 11. The push arm 11 is a "U-shaped" branch structure (see FIG. 2), whose two arms get close to or in touch with the end of the flexible arm 8 transversely through the ejection cavity 5 from both sides of the lancet core 2, respectively, thus forming a push-type trigger structure.

The two arms of the "U-shaped" branch structure of the push arm 11 are provided on the side towards the casing 1 with a barb 12, respectively. The casing 1 is provided on the side corresponding to each of the barbs 12 with one self-locking barb 13, respectively, which is located in downward path of the barb 12 (see FIG. 2). The two barbs 12 are engaged with the two self-locking barbs 13, thus forming a self-locking structure that appears after the trigger button 10 is pushed once.

The ejection cavity 5 is provided inside with two spaces 17 allowing the two arms of the "U-shaped" branch structure of the push arm 11 to move downwards (see the area circled by the double dotted line as indicated by the reference number 17 in FIG. 2). The Z direction of the space 17 is defined as a direction along which the push arm 11 moves downwards, the X direction parallel to axis of the needle 14, and the Y direction perpendicular to the X and Z directions. The protective bar 4 is provided at the end inside the ejection cavity 5 with a safety action portion, which is provided for the two spaces 17 with two safety feet 16 extended from the end of the protective bar 4. With the protective bar 4 assembled, the two safety feet 16 occupy the two spaces 17 in the Y direction, making the widths of the two spaces 17 in the Y direction both smaller than the width at which the push arm 11 of the "U-shaped" branch structure can be inserted, so as to prevent the push arm 11 from moving downwards to drive the barb 12 to be self-locked with the self-locking barb 13. With the protective bar 4 disassembled, the two safety feet 16 both withdraw from the two spaces 17, making the widths of the two spaces 17 in the Y direction bigger than or equal to the width at which the push arm 11 of the "U-shaped" branch structure can be inserted, so as to allow the push arm 11 to move downwards to drive the barb 12 to be self-locked with the self-locking barb 13. Thus, a safety structure of the trigger button is formed.

FIGS. 6-10 show the lancet core 2 and the protective bar 4 according to the examples of the present invention. These drawings clearly show details of each part of the lancet core 2 and the protective bar 4 as well as the connection relation in the assembly state.

Figure 4:
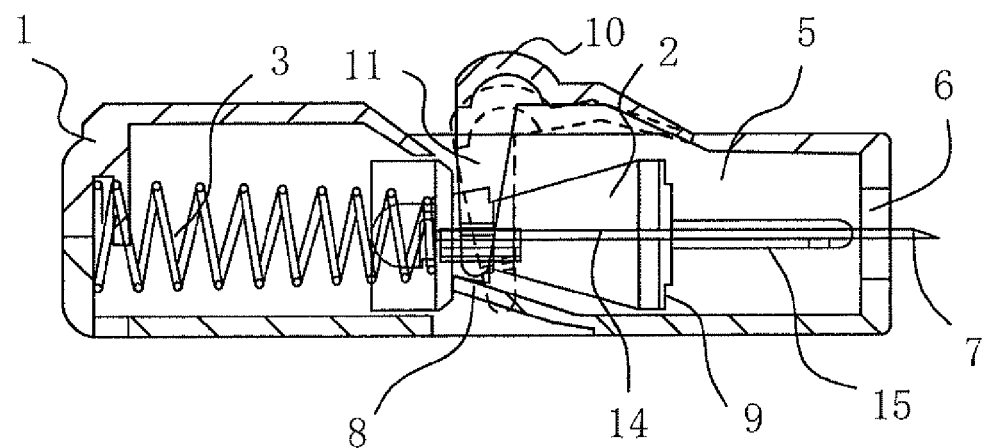
FIG. 4 is a front view of the product according to Example 1 of the present invention in the ejection state.
Figure 5:
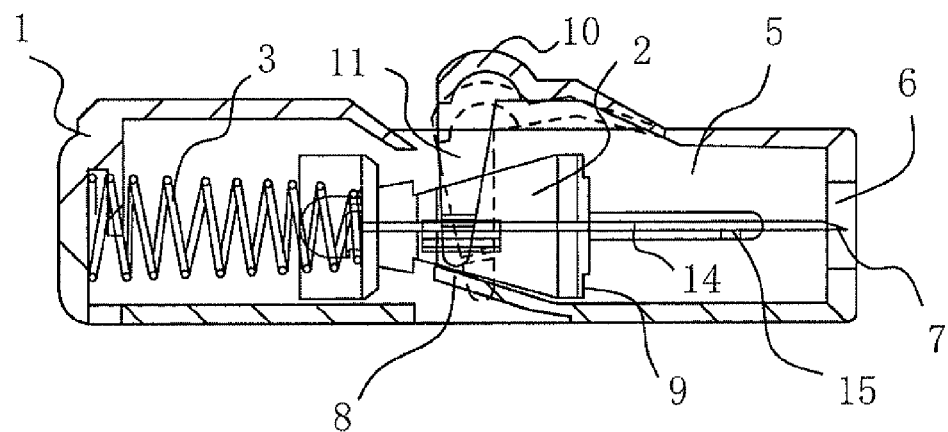
FIG. 5 is a front view of the product according to Example 1 of the present invention in the post-ejection state.
Figure 6:
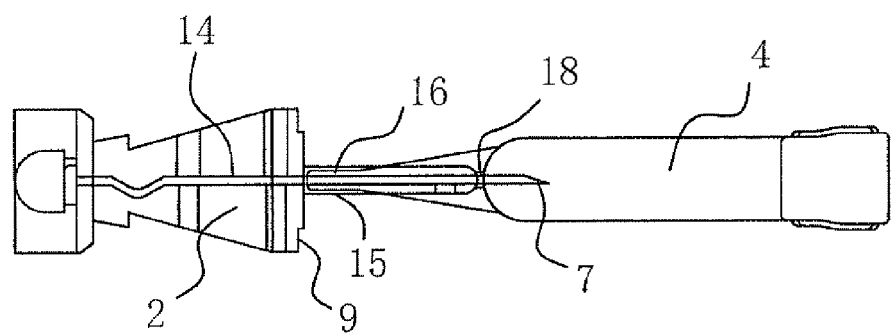
FIG. 6 is a front view of the lancet core and the protective bar of the product according to Example 1 of the present invention.
Figure 7:
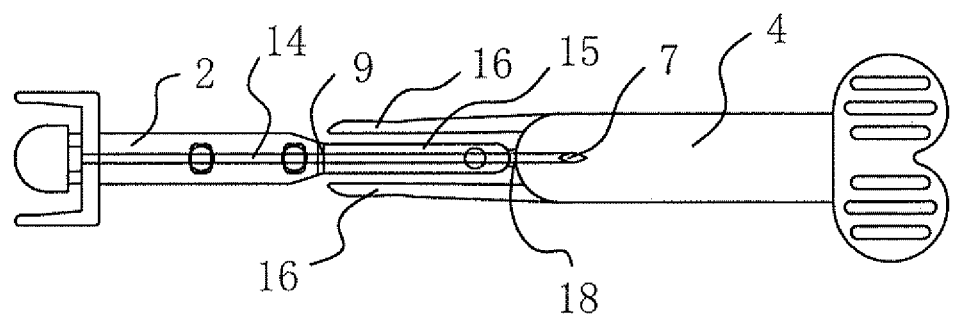
FIG. 7 is a top view of FIG. 6.
Figure 8:
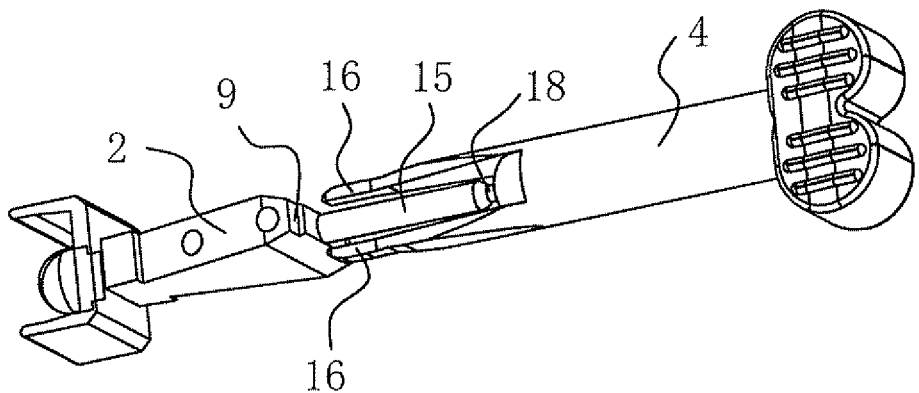
FIG. 8 is a stereoscopic drawing (1) of the lancet core and the protective bar of the product according to Example 1 of the present invention.
Figure 9:
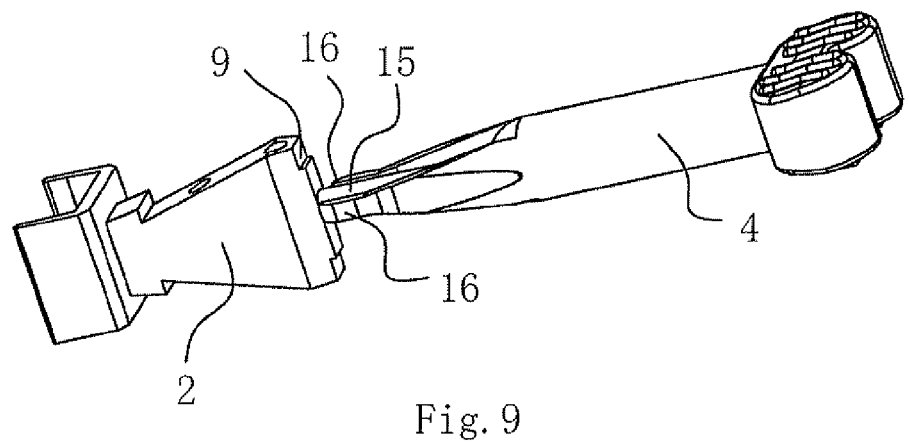
FIG. 9 is a stereoscopic drawing (2) of the lancet core and the protective bar of the product according to Example 1 of the present invention.
Figure 10:
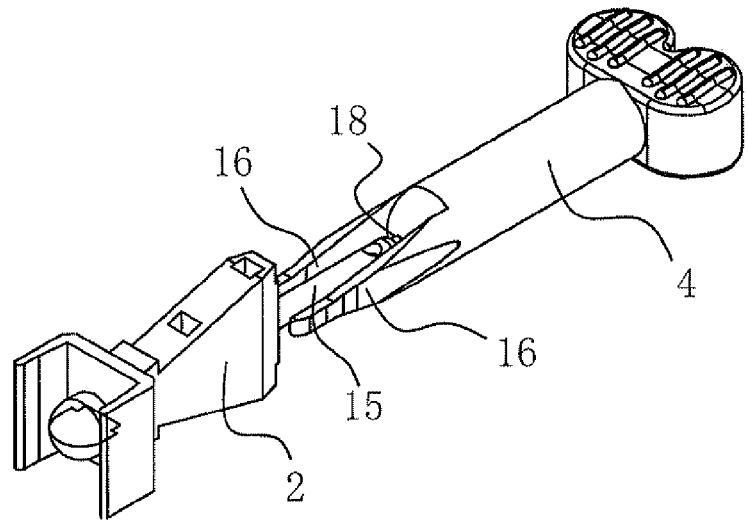
FIG. 10 is a stereoscopic drawing (3) of the lancet core and the protective bar of the product according to Example 1 of the present invention.

As shown in FIGS. 1-3, the present invention allows the lancet core to be assembled into the locking state of ready for ejection during manufacture of the blood lancet (or the lancet core is not assembled into the locking state of ready for ejection, but an action of pushing the protective bar 4 has to be added during application). In this state, since the protective bar 4 is not disassembled, and the trigger button 10 is in the safety protection state, an incorrect ejection will not occur. The medical care personnel only need to perform one action of twisting off the protective bar 4 during application to place the blood lancet in the ready-for-ejection state (see FIG. 2 for the action of twisting off the protective bar 4). When the trigger button 10 is pushed, the push arm 11 pushes the flexible arm 8 to make the lancet core 2 disengaged from the casing 1, and then the spring 3 pushes the lancet core 2 to eject (see FIG. 4). Meanwhile, because of movement of the push arm 11, the barb 12 exceeds the self-locking barb 13 when moving downwards (see FIG. 2). Therefore, during the rebounding process, the barb 12 enters the self-locking state by being locked at the self-locking barb 13 and cannot go back to the original state, causing the bayonet ejection structure to fail and be unreusable (see FIG. 5).

In this example, the core pillar 15 in the front of the lancet core 2 refers to a pillar of the lancet core 2 at its front position wrapping the needle 14. The sectional shape of the core pillar 15 is not defined strictly in the present invention, and can take any shape. However, the sectional shape is preferred to be of a cylinder or a prism in actual application, since such a design can make the protective bar 4 twisted off without causing any trouble. Otherwise, because the safety feet 16 are located at both sides of the core pillar 15, twisting the protective bar 4 will cause some troubles, and the protective bar 4 can only be removed by being pulled out. The prism includes a triangular prism, a quadrangular prism (typically a square prism), a multi-angular prism, and so on.

Figure 11:
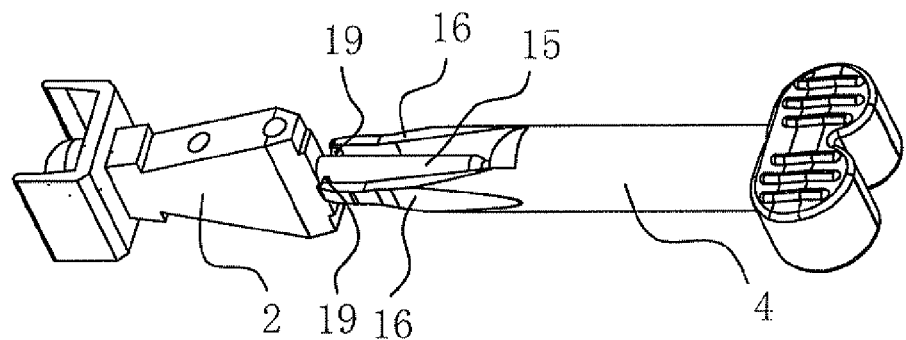
FIG. 11 is a stereoscopic drawing of Example 1 of the present invention where a connection rib is arranged between the core pillar and the safety foot.
Figure 12:
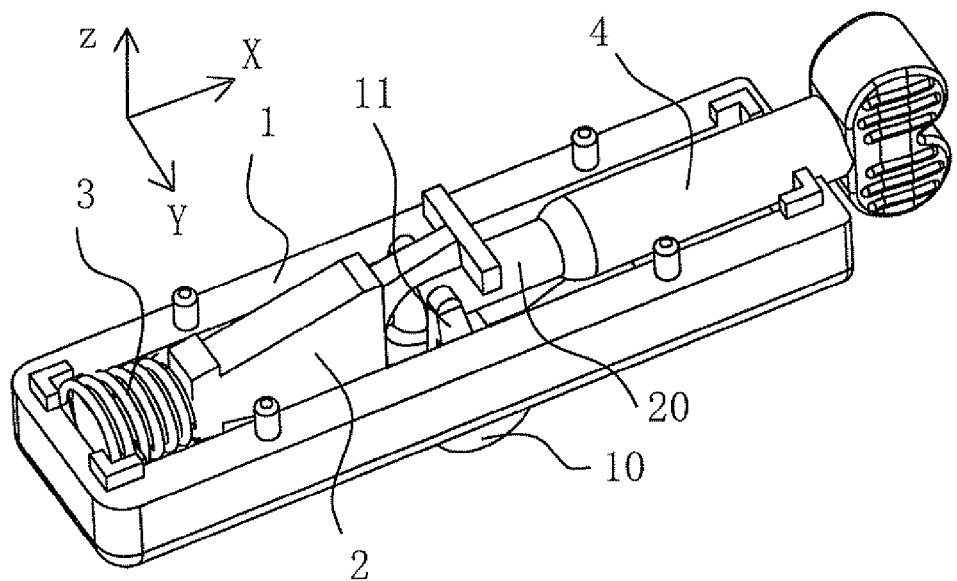
FIG. 12 is a stereoscopic drawing of the internal structure of the product according to Example 2 of the present invention.
Figure 13:
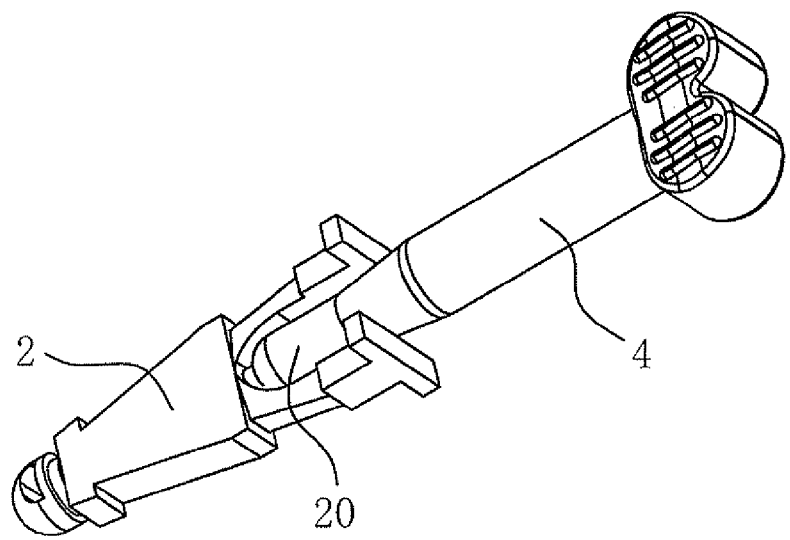
FIG. 13 is a stereoscopic drawing of the lancet core and the protective bar of the product according to Example 2 of the present invention.
Figure 14:
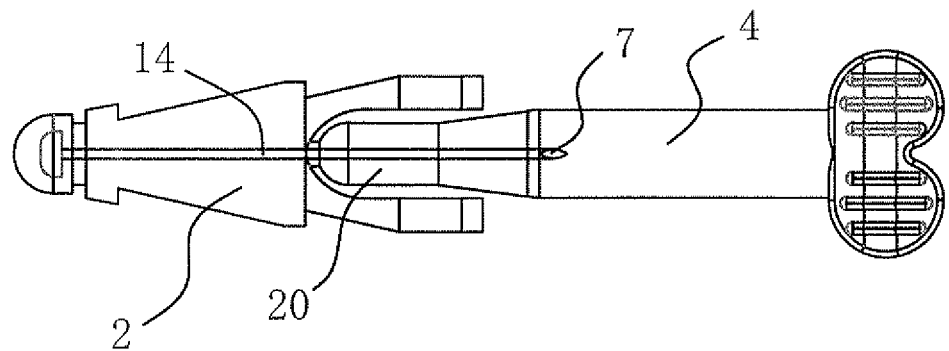
FIG. 14 is a front view of the lancet core and the protective bar of the product according to Example 2 of the present invention.
Figure 15:
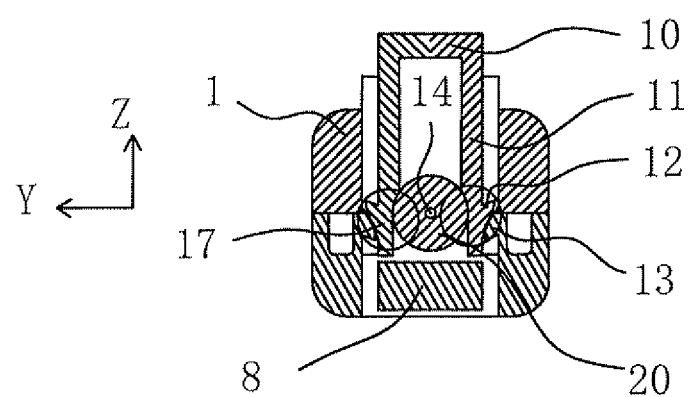
FIG. 15 is a sectional view of the safety structure of the trigger button according to Example 2 of the present invention.

In this example, for facilitating assembly, a connection rib 19 can be arranged between the core pillar 15 and the two safety feet 16, respectively, as shown in FIG. 11. The medical care personnel can twist broken the connection rib 19 when twisting the protective bar 4, and then twist off the protective bar 4. Alternatively, the connection rib 19 is not provided.

In this example, the flexible arm 8 is designed for locking the lancet core 2, and can take various forms, which will all fall within the extent of protection of the present invention so long as the lancet core 2 can be locked/released by engaging/disengaging the flexible arm 8 with/from the bayonet 9 on the lancet core 2 by making use of flexibility of the flexible arm 8. The flexible arm 8 is preferred to be slantly arranged with an orientation as shown in FIG. 1, and can also be arranged in the opposite direction with a hook hooked at the bayonet 9.

Example 2

A Safe Simple Disposable Automatic Blood Lancet

As shown in FIGS. 12-15, this example is different from Example 1 in the following aspects: The safety action portion is arranged for the two spaces 17, and refers to one safety jacket 20 extended from the end of the protective bar 4. The safety jacket 20 is muff-coupled in front of the lancet core 2 or with the needle 14. With the protective bar 4 assembled, the external edge of the safety jacket 20 occupies the two spaces 17 in the Y direction (see the direction as indicated by the coordinate in FIG. 15) (see the area circled by the double dotted line as indicated by the reference number 17 in FIG. 15), making the widths of the two spaces 17 in the Y direction both smaller than the width at which the push arm 11 of the "U-shaped" branch structure can be inserted, so as to prevent the push arm 11 from moving downwards to drive the barb 12 to be self-locked with the self-locking barb 13. With the protective bar 4 disassembled, the safety jacket 20 withdraws from the two spaces 17, making the widths of the two spaces 17 in the Y direction bigger than or equal to the width at which the push arm 11 of the "U-shaped" branch structure can be inserted, so as to allow the push arm 11 to move downwards to drive the barb 12 to be self-locked with the self-locking barb 13. Thus, the safety structure of the trigger button is formed. The other structures and principles are similar to those in Example 1, and will not be described again here.

Example 3

A Safe Simple Disposable Automatic Blood Lancet

Figure 16:
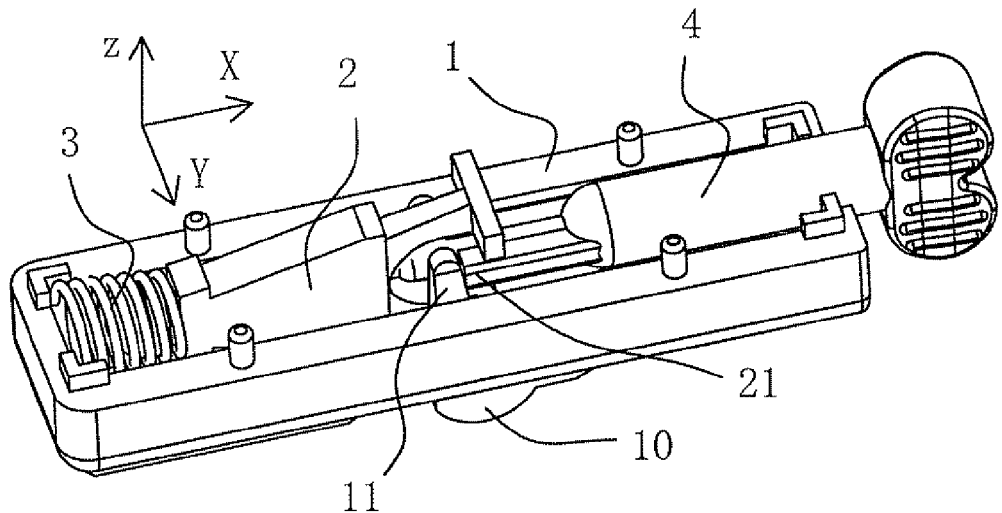
FIG. 16 is a stereoscopic drawing of the internal structure of the product according to Example 3 of the present invention.
Figure 17:
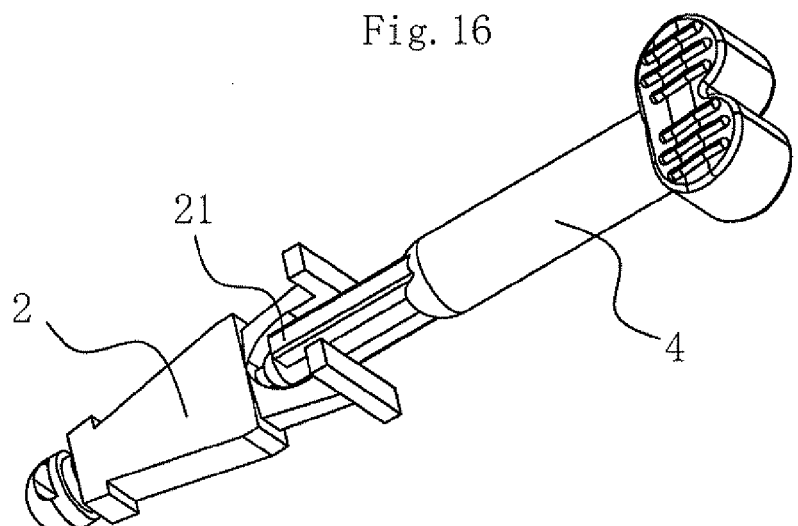
FIG. 17 is a stereoscopic drawing of the lancet core and the protective bar of the product according to Example 3 of the present invention.
Figure 18:
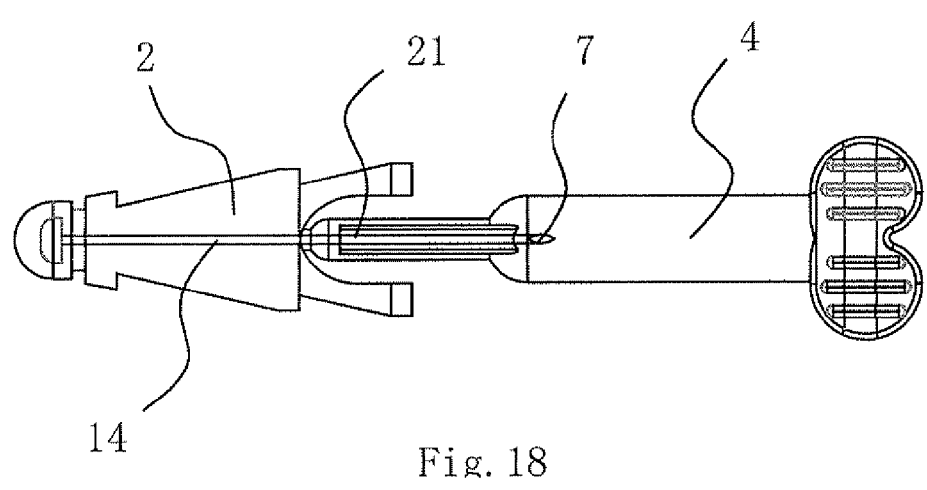
FIG. 18 is a front view of the lancet core and the protective bar of the product according to Example 3 of the present invention.

As shown in FIGS. 16-18, this example is different from Example 1 in the following aspects: The safety action portion is arranged for the two spaces 17, and refers to two safety wings 21 extended from the end of the protective bar 4. With the protective bar 4 assembled, the two safety wings 21 occupy the two spaces 17 in the X direction (see the direction as indicated by the coordinate in FIG. 16), making the widths of the two spaces 17 in the X direction both smaller than the width at which the push arm 11 of the "U-shaped" branch structure can be inserted, so as to prevent the push arm 11 from moving downwards to drive the barb 12 to be self-locked with the self-locking barb 13. With the protective bar 4 disassembled, the two safety wings 21 both withdraw from the two spaces 17, making the widths of the two spaces 17 in the X direction bigger than or equal to the width at which the push arm 11 of the "U-shaped" branch structure can be inserted, so as to allow the push arm 11 to move downwards to drive the barb 12 to be self-locked with the self-locking barb 13. Thus, a safety structure of the trigger button is formed. The other structures and principles are similar to those in Example 1, and will not be described again here.

Example 4

A Safe Simple Disposable Automatic Blood Lancet

Figure 19:
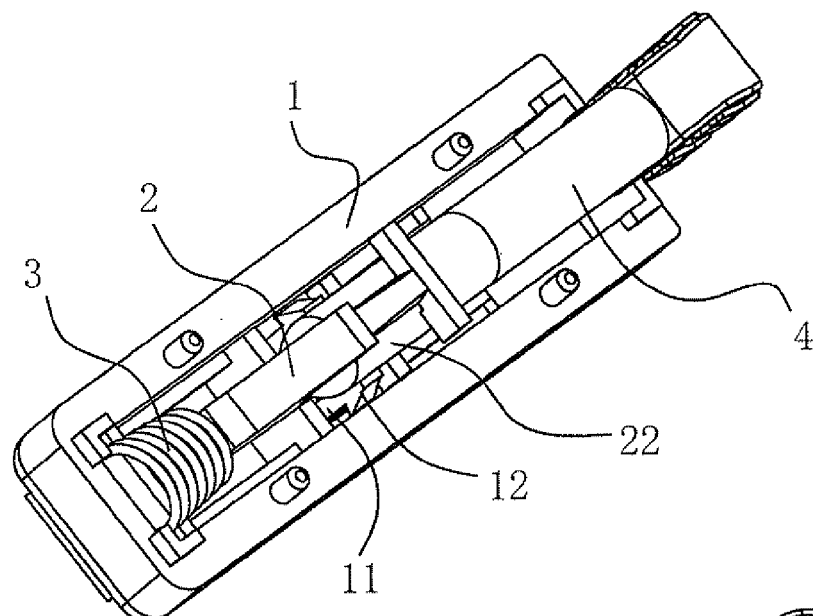
FIG. 19 is a stereoscopic drawing of the internal structure of the product according to Example 4 of the present invention.
Figure 20:
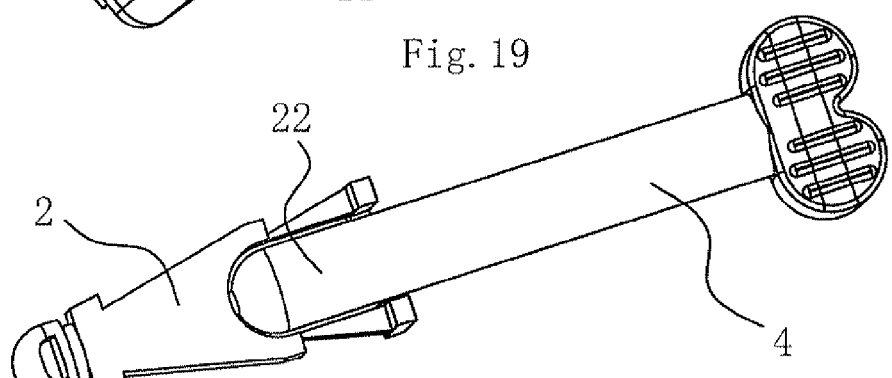
FIG. 20 is a stereoscopic drawing of the lancet core and the protective bar of the product according to Example 4 of the present invention.
Figure 21:
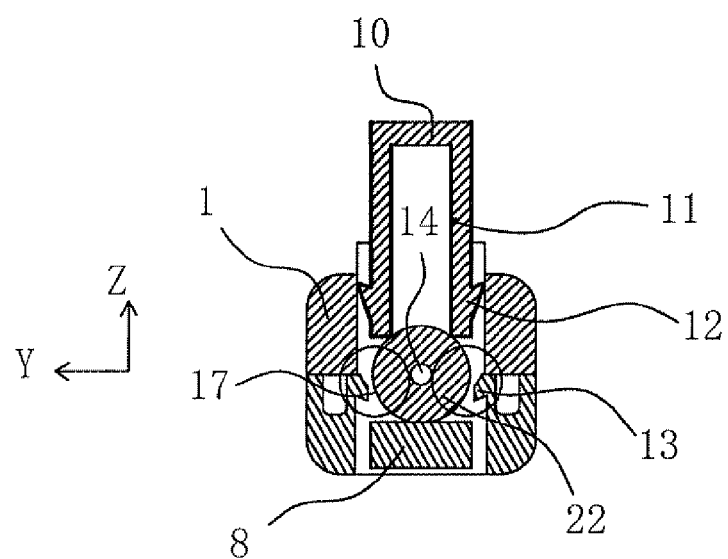
FIG. 21 is a front view of the lancet core and the protective bar of the product according to Example 4 of the present invention.

As shown in FIGS. 19-21, this example is different from Example 1 in the following aspects: The safety action portion is arranged for the two spaces 17, and refers to one safety bolt 22 extended from the end of the protective bar 4. The safety bolt 22 is muff-coupled in front of the lancet core 2 or with the needle 14. With the protective bar 4 assembled, the safety bolt 22 occupies the two spaces 17 in the Z direction (see the direction as indicated by the coordinate in FIG. 21) (see the area circled by the double dotted line as indicated by the reference number 17 in FIG. 21), making the two spaces (17) blocked in the Z direction, so as to prevent the push arm 11 from moving downwards to drive the barb 12 to be self-locked with the self-locking barb 13. With the protective bar 4 disassembled, the safety bolt 22 withdraws from the two spaces 17, making the two spaces (17) vacant in the Z direction, so as to allow the barb 12 to be self-locked with the self-locking barb 13 with the push arm 11 moving downwards. Thus, a safety structure of the trigger button is formed. The other structures and principles are similar to those in Example 1, and will not be described again here, Example 5

A Safe Simple Disposable Automatic Blood Lancet

Figure 22:
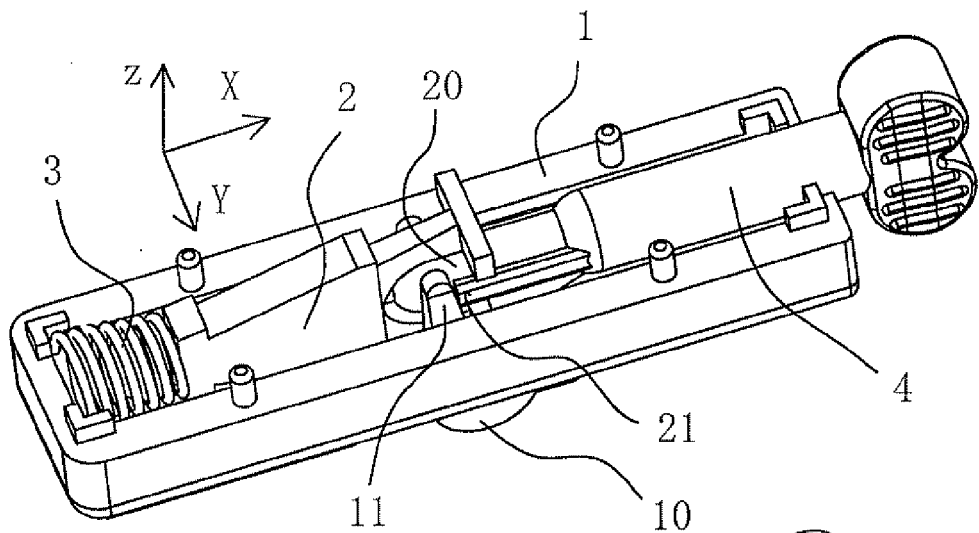
FIG. 22 is a stereoscopic drawing of the internal structure of the product according to Example 5 of the present invention.
Figure 23:
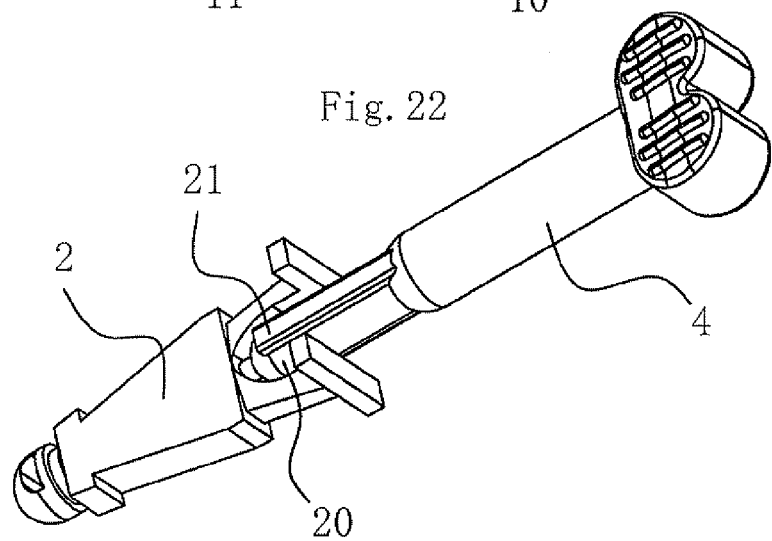
FIG. 23 is a stereoscopic drawing of the lancet core and the protective bar of the product according to Example 5 of the present invention.
Figure 24:
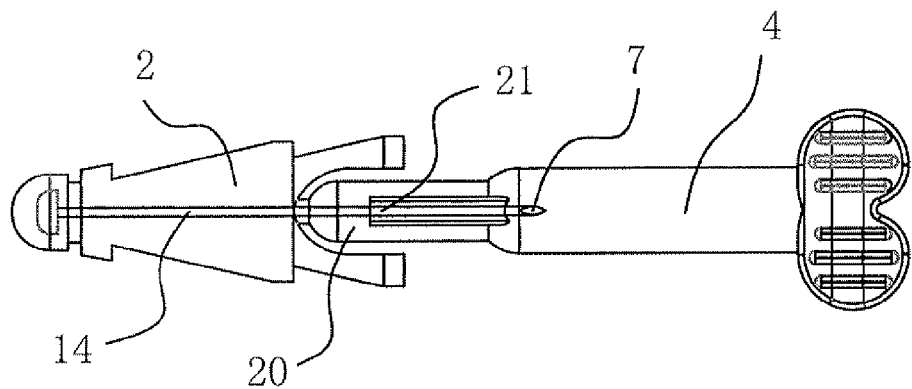
FIG. 24 is a front view of the lancet core and the protective bar of the product according to Example 5 of the present invention.

As shown in FIGS. 22-24, this example is actually a combination of the structures of the safety action portions of Examples 2 and 3. Its safety action portion is specifically composed of one safety jacket 20 and two safety wings 21 extended from the end of the protective bar 4. The two safety wings 21 are arranged at both sides of the safety jacket 20. With the protective bar 4 assembled, the two safety jacket 20 occupy the two spaces 17 in the Y direction, and the two safety wings 21 in the X direction, making the widths of the two spaces 17 in the Y and X directions both smaller than the width at which the push arm 11 of the "U-shaped" branch structure can be inserted, so as to prevent the push arm 11 from moving downwards to drive the barb 12 to be self-locked with the self-locking barb 13. With the protective bar 4 disassembled, both the safety jacket 20 and the safety wings 21 withdraw from the two spaces 17, making the widths of the two spaces 17 in the Y and X directions bigger than or equal to the width at which the push arm 11 of the "U-shaped" branch structure can be inserted, so as to allow the push arm 11 to move downwards to drive the barb 12 to be self-locked with the self-locking barb 13. Thus, a safety structure of the trigger button is formed. The other structures and principles are similar to those in Example 1, and will not be described again here.

Example 6

A Safe Simple Disposable Automatic Blood Lancet

This example is actually a combination of the structures of the safety action portions of Examples 1 and 3 (not shown in the drawings). Its safety action portion is specifically composed of two safety feet 16 and two safety wings 21 extended from the end of the protective bar 4. With the protective bar 4 assembled, the two safety feet 16 occupy the two spaces 17 in the Y direction, and the two safety wings 21 in the X direction, making the widths of the two spaces 17 in the Y and X directions both smaller than the width at which the push arm 11 of the "U-shaped" branch structure can be inserted, so as to prevent the push arm 11 from moving downwards to drive the barb 12 to be self-locked with the self-locking barb 13. With the protective bar 4 disassembled, both the two safety feet 16 and the two safety wings 21 withdraw from the two spaces 17, making the widths of the two spaces 17 in the Y and X directions bigger than or equal to the width at which the push arm 11 of the "U-shaped" branch structure can be inserted, so as to allow the push arm 11 to move downwards to drive the barb 12 to be self-locked with the self-locking barb 13. Thus, a safety structure of the trigger button is formed.

According to Examples 1-6 as described above, those skilled in the art can fully understand and implement the technical solutions that the space 17 is occupied by the safety action portion in the combined X and Z directions as well as in the combined Y and Z directions. Therefore, these cases will not be described here in detail.

The examples as described above are used only for explaining technical concept and characteristics of the present invention. They are provided rather to make those skilled in the art understand the present invention and implement it, than to limit the extent of protection of the present invention. All equivalent changes or modifications according to the spirit of the present invention should fall within the extent of protection of the present invention.

What is claimed is:

1. A safe simple disposable automatic blood lancet, comprising:
   a casing, the casing forming an ejection cavity, the casing having a pinhole at one end thereof;
   a lancet core that elongates along an X direction defined as an axial direction, the lancet core being arranged inside the ejection cavity and having at one end thereof a protective bar, one end of the protective bar protruding out of the pinhole of the casing; and
   a spring,
   the lancet core being provided with a needle therein, a needle point of the needle being located inside the protective bar and oriented towards the pinhole; the protective bar and the lancet core being connected by muff-coupling or via a neck that can be twisted broken to enable a demountable connection; and the spring being arranged at the other end of the lancet core, thus forming an ejection structure with which the spring can push the lancet core to move;
   a part of the casing extending into the ejection cavity to form a flexible arm used for locking the lancet core; and the lancet core being provided with a bayonet corresponding to the flexible arm, the flexible arm being configured to engage at an end thereof with the bayonet, thus forming a locking structure in a ready-for-ejection state upon the lancet core compressing the spring;
   the casing being provided with a trigger button, the trigger button being formed by an extension of the casing or an independent member mounted on the casing; and the trigger button being provided with a push arm, the push arm transversely passing through the ejection cavity to get close to or in touch with the end of the flexible arm, thus forming a push-type trigger structure; and
   the trigger button being provided on the push arm with a barb; the casing being provided with a self-locking barb corresponding to the barb and being located in a downward path of the barb, thus forming a self-locking structure upon the barb being engaged with the self-locking barb after the trigger button is pushed once;
   wherein:
   the ejection cavity encloses a space that allows the push arm to move downwards along a Z direction that is perpendicular to the X direction; the space being 3-dimensional and extending in the X direction, the Z direction, and a Y direction that is perpendicular to the X and Z directions, and the protective bar is provided with a safety action portion at the other end thereof that is inside the ejection cavity;
   with the protective bar assembled, the safety action portion occupies the space in the X, Y or Z direction or simultaneously in arbitrary two of the X, Y and Z directions, and prevents the push arm from moving downwards to drive the barb to be self-locked with the self-locking barb; with the protective bar disassembled, the safety action portion withdraws from the space and allows the push arm to move downwards to drive the barb to be self-locked with the self-locking barb; and thus a safety structure of the trigger button is formed.

2. The safe simple disposable automatic blood lancet according to claim 1, wherein the safety action portion is composed of a safety foot extended in the X direction from the other end of the protective bar; with the protective bar assembled, the safety foot occupies the space in the Y direction, making a width of the space in the Y direction smaller than a width required for the push arm to move downwards so as to prevent the push arm from moving downwards along the Z direction; with the protective bar disassembled, the safety foot withdraws from the space, making the width of the space in the Y direction bigger than or equal to the width required for the push arm to move downwards along the Z direction so as to allow the push arm to move downwards along the Z direction.

3. The safe simple disposable automatic blood lancet according to claim 1, wherein the safety action portion is composed of a safety jacket extended in the X direction from the other end of the protective bar; with the protective bar assembled, the safety jacket occupies the space in the Y direction, making a width of the space in the Y direction smaller than a width required for the push arm to move downwards along the Z direction so as to prevent the push arm from moving downwards along the Z direction; with the protective bar disassembled, the safety jacket withdraws from the space, making the width of the space in the Y direction bigger than or equal to the width required for the push arm to move downwards along the Z direction so as to allow the push arm to move downwards along the Z direction.

4. The safe simple disposable automatic blood lancet according to claim 1, wherein the safety action portion is composed of a safety wing extended in the X direction from the other end of the protective bar; with the protective bar assembled, the safety wing occupies the space in the X direction, making a width of the space in the X direction smaller than a width required for the push arm to move downwards along the Z direction so as to prevent the push arm from moving downwards along the Z direction; with the protective bar disassembled, the safety wing withdraws from the space, making the width of the space in the X direction bigger than or equal to the width required for the push arm to move downwards along the Z direction so as to allow the push arm to move downwards along the Z direction.

5. The safe simple disposable automatic blood lancet according to claim 1, wherein the safety action portion is composed of a safety bolt extended in the X direction from the other end of the protective bar; with the protective bar assembled, the safety bolt occupies the space in the Z direction, making the space blocked in the Z direction so as to prevent the push arm from moving downwards along the Z direction; with the protective bar disassembled, the safety bolt withdraws from the space, making the space vacant in the Z direction so as to allow the push arm to move downwards along the Z direction.

6. The safe simple disposable automatic blood lancet according to claim 1, wherein the safety action portion is composed of a safety jacket and a safety wing extended in the X direction from the other end of the protective bar; with the protective bar assembled, the safety jacket occupies the space in the Y direction, and the safety wing in the X direction, making widths of the space in the Y and X directions both smaller than widths required for the push arm to move downwards along the Z direction so as to prevent the push arm from moving downwards along the Z direction; with the protective bar disassembled, both the safety jacket and the safety wing withdraw from the space, making the widths of the space in the Y and X directions bigger than or equal to the widths required for the push arm to move downwards along the Z direction so as to allow the push arm to move downwards along the Z direction.

7. The safe simple disposable automatic blood lancet according to claim 1, wherein the safety action portion is composed of a safety foot and a safety wing extended in the X direction from the other end of the protective bar; with the protective bar assembled, the safety foot occupies the space in the Y direction, and the safety wing in the X direction, making widths of the space in the Y and X directions both smaller than widths required for the push arm to move downwards along the Z direction so as to prevent the push arm from moving downwards along the Z direction; with the protective bar disassembled, both the safety foot and the safety wing withdraw from the space, making the widths of the space in the Y and X directions bigger than or equal to the widths required for the push arm to move downwards along the Z direction so as to allow the push arm to move downwards along the Z direction.

8. The safe simple disposable automatic blood lancet according to claim 1, wherein the push arm of the trigger button is a "U-shaped" branch structure having two arms that get close to or in touch with the end of the flexible arm transversely through the ejection cavity from both sides of the lancet core, respectively; the two arms are provided on a side towards the casing with the barb, respectively; and the casing is provided on a side corresponding to each of the barbs with one self-locking barb, respectively.

9. The safe simple disposable automatic blood lancet according to claim 1, wherein the flexible arm is slantly arranged towards inside of the ejection cavity.

* * * * *